(12) United States Patent
Davis

(10) Patent No.: US 6,736,850 B2
(45) Date of Patent: May 18, 2004

(54) VERTEBRAL PSEUDO ARTHROSIS DEVICE AND METHOD

(75) Inventor: Reginald J. Davis, Cockeysville, MD (US)

(73) Assignee: Spinal Concepts, Inc., Austin, TX (US)

( * ) Notice: Subject to any disclaimer, the term of this patent is extended or adjusted under 35 U.S.C. 154(b) by 0 days.

(21) Appl. No.: 10/035,052

(22) Filed: Dec. 28, 2001

(65) Prior Publication Data

US 2003/0208274 A1 Nov. 6, 2003

(51) Int. Cl.$^7$ .................................................. A61F 2/44
(52) U.S. Cl. ........................... 623/17.16; 623/17.12; 623/17.13; 623/17.15
(58) Field of Search ........................ 623/17.13, 17.16, 623/17.12, 17.11, 17.15

(56) References Cited

U.S. PATENT DOCUMENTS

| | | |
|---|---|---|
| 3,867,728 A | 2/1975 | Stubstad et al. .................. 3/1 |
| 4,309,777 A | 1/1982 | Patil |
| 4,349,921 A | 9/1982 | Kuntz |
| 4,759,766 A | 7/1988 | Buettner-Janz et al. |
| 4,759,769 A | 7/1988 | Hedman et al. |
| 4,772,287 A | 9/1988 | Ray et al. |
| 4,863,477 A | 9/1989 | Monson |
| 4,911,718 A | 3/1990 | Lee et al. |
| 4,932,975 A | 6/1990 | Main et al. |
| 4,946,378 A | 8/1990 | Hirayama et al. |
| 5,047,055 A | 9/1991 | Bao et al. |
| 5,071,437 A | 12/1991 | Steffee ......................... 623/17 |
| 5,108,438 A | 4/1992 | Stone |
| 5,123,926 A * | 6/1992 | Pisharodi ..................... 623/17 |
| 5,171,281 A | 12/1992 | Parsons et al. |
| 5,192,326 A * | 3/1993 | Bao et al. ..................... 623/17 |
| 5,246,458 A | 9/1993 | Graham |
| 5,258,031 A | 11/1993 | Salib et al. |
| 5,306,307 A | 4/1994 | Senter et al. |
| 5,306,309 A | 4/1994 | Wagner et al. |
| 5,314,477 A | 5/1994 | Marnay |
| 5,320,644 A | 6/1994 | Baumgartner ................ 623/17 |
| 5,401,269 A | 3/1995 | Buttner-Janz et al. |
| 5,425,773 A * | 6/1995 | Boyd et al. .................... 623/17 |
| 5,458,642 A * | 10/1995 | Beer et al. ..................... 623/17 |
| 5,458,643 A | 10/1995 | Oka et al. |
| 5,514,180 A | 5/1996 | Heggeness et al. |
| 5,522,899 A | 6/1996 | Michelson .................... 623/17 |
| 5,534,028 A | 7/1996 | Bao et al. |
| 5,534,030 A | 7/1996 | Navarro et al. |
| 5,556,431 A | 9/1996 | Buttner-Janz |
| 5,562,738 A | 10/1996 | Boyd et al. |

(List continued on next page.)

FOREIGN PATENT DOCUMENTS

| | | |
|---|---|---|
| FR | 2799638 | 4/2001 |
| WO | 00/04851 | 2/2000 |
| WO | 00/74606 | 12/2000 |

OTHER PUBLICATIONS

Manasas et al., Pub. No. US2002/0128714 A1, Pub. Date Sep. 12, 2002, Orthopedic Implant and Method of Making Metal Articles.*
Husson, Pub. No. US2003/0018390 A1, Pub. Date Jan. 23, 2003, Intervertebral Prosthesis.*
Pub. No. 2002/0130112 A1, Pub. Date: Sep. 19, 2002, application No. 09/874,679, filed Jun. 05, 2001, Manasas et al.*
International Search Report, Application No.PCT/US02/41425, mailed May 23, 2003.

*Primary Examiner*—Bruce Snow
*Assistant Examiner*—Cheryl Miller
(74) *Attorney, Agent, or Firm*—Beth A. Vrioni

(57) ABSTRACT

A pseudo arthrosis device disposed in a patient between two adjacent vertebrae. The device has an enclosure with a plurality of compressible flexible members packed longitudinally therein. The enclosure is attached to at least one of the adjacent vertebrae. A method of use is disclosed.

20 Claims, 3 Drawing Sheets

U.S. PATENT DOCUMENTS

| | | | | |
|---|---|---|---|---|
| 5,674,294 | A | 10/1997 | Bainville et al. | |
| 5,676,701 | A | 10/1997 | Yuan et al. | |
| 5,676,702 | A * | 10/1997 | Ratron | 623/17 |
| 5,683,464 | A | 11/1997 | Wagner et al. | |
| 5,683,465 | A | 11/1997 | Shinn et al. | |
| 5,702,450 | A | 12/1997 | Bisserie | |
| 5,755,797 | A | 5/1998 | Baumgartner | |
| 5,782,832 | A * | 7/1998 | Larsen et al. | 606/61 |
| 5,800,549 | A | 9/1998 | Bao et al. | |
| 5,824,093 | A | 10/1998 | Ray et al. | |
| 5,824,094 | A | 10/1998 | Serhan et al. | |
| 5,827,328 | A | 10/1998 | Buttermann | |
| 5,861,041 | A | 1/1999 | Tienboon | |
| 5,865,846 | A | 2/1999 | Bryan et al. | |
| 5,888,220 | A | 3/1999 | Felt et al. | |
| 5,888,226 | A | 3/1999 | Rogozinski | |
| 5,893,889 | A | 4/1999 | Harrington | |
| 5,895,427 | A | 4/1999 | Kuslich et al. | 623/17 |
| 5,895,428 | A | 4/1999 | Berry | |
| 5,899,941 | A | 5/1999 | Nishijima et al. | |
| 5,961,554 | A | 10/1999 | Janson et al. | 623/17 |
| 5,976,186 | A | 11/1999 | Bao et al. | 623/17 |
| 5,984,967 | A | 11/1999 | Zdeblick et al. | 623/17 |
| 6,001,130 | A | 12/1999 | Bryan et al. | |
| 6,019,792 | A | 2/2000 | Cauthen | |
| 6,022,376 | A | 2/2000 | Assell et al. | |
| 6,039,763 | A | 3/2000 | Shelokov | |
| 6,093,205 | A | 7/2000 | McLeod et al. | |
| 6,110,210 | A | 8/2000 | Norton et al. | |
| 6,113,637 | A | 9/2000 | Gill et al. | |
| 6,132,465 | A | 10/2000 | Ray et al. | |
| 6,136,031 | A | 10/2000 | Middleton | |
| 6,139,579 | A | 10/2000 | Steffee et al. | |
| 6,146,421 | A | 11/2000 | Gordon et al. | |
| 6,156,067 | A | 12/2000 | Bryan et al. | |
| 6,162,252 | A | 12/2000 | Kuras et al. | 623/17.16 |
| 6,165,218 | A | 12/2000 | Husson et al. | |
| 6,179,874 | B1 | 1/2001 | Cauthen | |
| 6,187,048 | B1 | 2/2001 | Milner et al. | |
| 6,206,924 | B1 | 3/2001 | Timm | 623/17.16 |
| 6,214,049 | B1 | 4/2001 | Gayer et al. | 623/16.11 |
| 6,228,118 | B1 | 5/2001 | Gordon | |
| 6,296,664 | B1 | 10/2001 | Middleton | |
| 6,315,797 | B1 | 11/2001 | Middleton | |
| 6,348,071 | B1 | 2/2002 | Steffee et al. | |
| 6,368,350 | B1 | 4/2002 | Erickson et al. | |
| 6,371,990 | B1 * | 4/2002 | Ferree | 623/17.16 |
| 6,395,032 | B1 | 5/2002 | Gauchet | |
| 6,395,034 | B1 | 5/2002 | Suddaby | |
| 6,402,784 | B1 | 6/2002 | Wardlaw | |
| 6,402,785 | B1 | 6/2002 | Zdeblick et al. | |
| 6,419,704 | B1 | 7/2002 | Ferree | |
| 6,440,168 | B1 | 8/2002 | Cauthen | |
| 6,478,822 | B1 | 11/2002 | Leroux et al. | |
| 6,482,234 | B1 * | 11/2002 | Weber et al. | 623/17.12 |
| 6,520,996 | B1 * | 2/2003 | Manasas et al. | 623/23.5 |

* cited by examiner

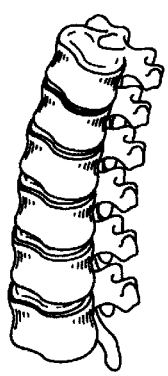 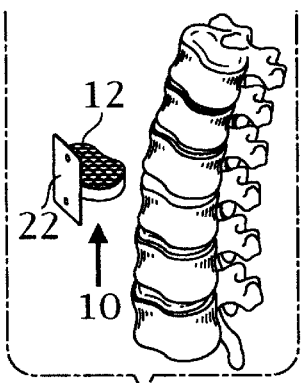 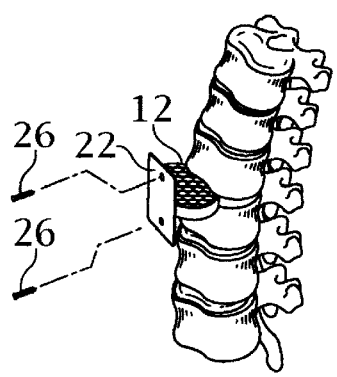 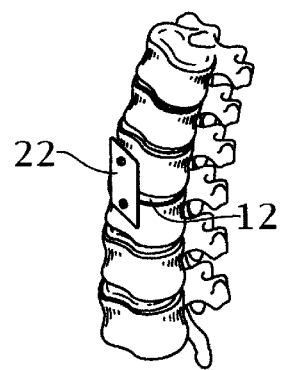
Fig 8    Fig 9    Fig 10    Fig 11
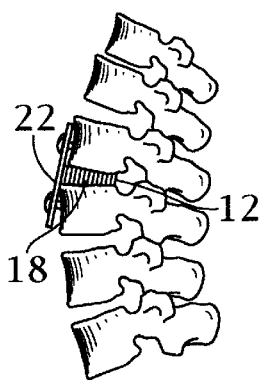 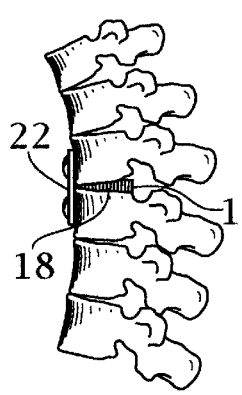 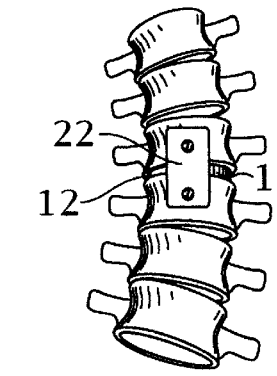 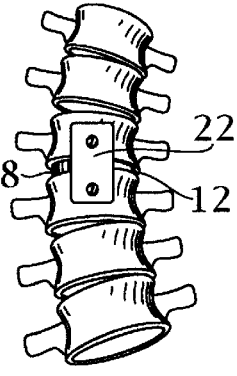
Fig 12    Fig 13    Fig 14    Fig 15
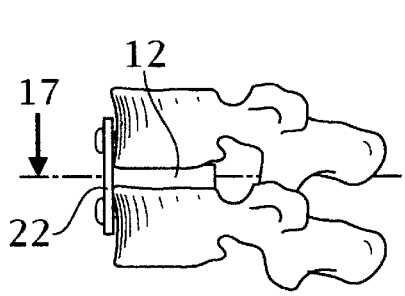 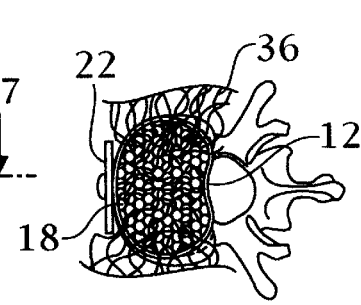 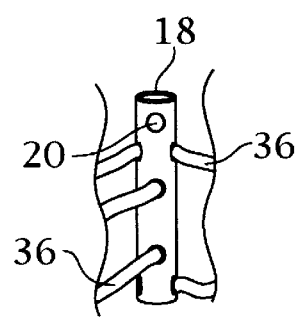
Fig 16    Fig 17    Fig 18

VERTEBRAL PSEUDO ARTHROSIS DEVICE AND METHOD

BACKGROUND OF THE INVENTION

1. Field of the Invention

The present invention relates to a device to alleviate problems in the spine and more particularly to a device to replace a damaged spinal disc and promote fibrous ingrowth.

2. Description of Related Art

Back pain and spinal disorders are very common human problems. One of the major causes of these problems are damage to and degeneration of spinal discs.

The spinal disc is a shock-absorbing structure in the spaces between each vertebra in the spine. Due to age or accident, these discs deteriorate. As a result, the shock-absorbing capacity is diminished and the adjacent vertebrae contact each other. This results in wear and tear on the vertebrae and pain to the neck and back of the person.

Non-surgical treatment to reduce the pain include rest, heat, medication, physical therapy and chiropractic manipulation. Unfortunately, there are a significant number of patients for whom these treatments are unsatisfactory.

Surgical treatment usually consists of spinal fusion. However, the success rate of spinal fusion ranges from approximately 50%–90%. Even successful spinal fusion often results in stiffness and decreased mobility of the patient and stress on the spine which often produces new problems.

Because of these problems with spinal fusion, alternate treatments have been investigated. Just as there are hip and knee replacement, the concept of spinal disc replacement has been considered.

Stubstad et al in U.S. Pat. No. 3,867,728, disclosed a number of alternate embodiments. One version of the prosthesis includes a plurality of flexible, curved, bar-like elements lying side by side to occupy the interior space of a natural disc. It provides resistance to compressive forces imposed on the spine and preserves the natural flexibility of the spine.

Steffee in U.S. Pat. No. 5,071,437, disclosed an artificial disc comprised of an upper and lower flat rigid plate with a flat polyolefin rubber core interposed between the plates. Protuberances extend outwardly from the exposed surfaces of the plates for engagement with vertebrae above and below the plates. A porous coating covers the exposed surfaces of the plates.

In U.S. Pat. No. 5,320,644, Baumgartner disclosed an intervertebral disk prosthesis which imitates a natural disk. It is made of one piece from a strong, elastically deformable material such as titanium or plastic material and comprises slits at a right angle to the connecting axis which partially overlap. The overlapping regions of adjacent slits form parts of leaf springs for transmission of forces.

In U.S. Pat. No. 5,522,899, Michelon disclosed an artificial spinal fusion implant, placed within the spinal disc space, and stabilizing the spinal segment.

In U.S. Pat. No. 5,961,554, Janson et al disclosed an intervertebral spacer employing a plurality of fused, generally spherical beads of a biologically inert material (preferably titanium or titanium alloy).

Bao et al, in U.S. Pat. No. 5,976,181 disclose a prosthetic intervertebral disc nucleus to be implanted in the cavity in the spine. The implant is an elongate, partially hydrated hydrogel.

Kuras et al, in U.S. Pat. No. 6,162,252 disclose a spinal prosthesis to replace a damaged spinal disc. A body of elastomeric material is bonded to upper and lower rigid plates. The elastomeric core is a polyolefin rubber.

In U.S. Pat. No. 6,206,924 B1, Timm disclosed a three-dimensional geometric porous engineered structure for use as a bone mass replacement device.

In U.S. Pat. No. 6,214,049 B1, Gayer et al disclosed a mesh of fibrillar wires formed on an implant device. An osteoinductive coating is then formed on the wires and implant device. The combination of the coating and the fibrillar wool or prongs should allow for optimal osteointegration and physiologic load distribution of an implant device.

Although there has been some progress in recent years, most of the devices known to date have not been generally accepted and there is a need for a comparatively simple, yet effective, device.

BRIEF SUMMARY OF THE INVENTION

It is an object of the present invention to provide a relatively inexpensive, simple device which is easily inserted into the spine to replace a damaged or degenerated disc.

It is a further object of the present invention to provide a replacement device which is compatible with the human body.

It is another object of the present invention to provide a replacement device which supports the growth of body fibers from the patient to incorporate the device naturally into the patient so that the body repairs itself.

In accordance with the teachings of the present invention, there is disclosed a pseudo arthrosis device disposed in a patient to support an intervertebral space between two adjacent vertebrae. The device has an enclosure having a plurality of compressible, flexible members packed longitudinally therein. The enclosure is disposed between the adjacent vertebrae. Means are provided for attaching the enclosure to at least one of the adjacent vertebrae.

In further accordance with the teachings of the present invention there is disclosed a pseudo arthrosis device disposed in a patient to support an intervertebral space between two adjacent vertebrae. The device has an enclosure formed from a flexible permeable material. A plurality of compressible flexible elongated hollow tubes are packed longitudinally within the enclosure. Each hollow tube has a plurality of spaced-apart perforations formed therein. Means are provided for attaching the enclosure to at least one of the adjacent vertebra. the enclosure is received in the intervertebral space and the hollow tubes are disposed between the adjacent vertebrae.

In another aspect, there is disclosed a method of replacing a damaged spinal disc between two adjacent vertebrae in a patient. The damaged spinal disc is removed. A pseudo arthrosis device is provided having an enclosure. A plurality of compressible, flexible members are packed longitudinally within the enclosure. At least one tab is connected to the enclosure. The pseudo arthrosis device is inserted between the adjacent vertebrae wherein the compressible, flexible members are disposed longitudinally between the adjacent vertebrae. The at least one tab is attached to at least one of the adjacent vertebrae to secure the enclosure between the adjacent vertebrae. In this manner, the pseudo arthrosis device replaces the damaged spinal disc.

These and other objects of the present invention will become apparent from a reading of the following specification taken in conjunction with the enclosed drawings.

BRIEF DESCRIPTION OF THE DRAWINGS

FIGS. 8–11 are a sequence of views showing the method of using the device of the present invention.

FIG. 8 is a view showing removable of the damaged disc.

FIG. 9 is a view showing the present invention to be inserted into the spine where the damaged disc was removed.

FIG. 10 is a view showing the present invention being inserted into the spine.

FIG. 11 is a view showing the present invention received in the spine with the screws holding the tab in place.

FIG. 12 is a partial cutaway view showing compression of the present invention when the patient bends backwardly.

FIG. 13 is a partial cutaway view showing compression of the present invention when the patient bends forwardly.

FIG. 14 is a partial cutaway view showing compression of the present invention when the patient leans laterally to the right.

FIG. 15 is a partial cutaway view showing compression of the present invention when the patient leans laterally to the left.

FIG. 16 is an enlarged view showing the present invention disposed in the spine.

FIG. 17 is a cross-section view taken along the lines 17—17 of FIG. 16 showing fibrous growth.

FIG. 18 is an enlarged view of one of the flexible members showing fibrous growth.

DESCRIPTION OF THE PREFERRED EMBODIMENTS

Figure 1:
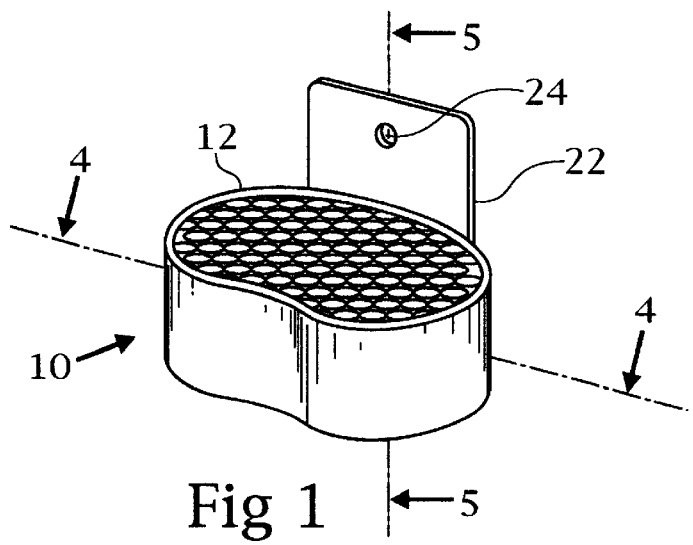
FIG. 1 is a perspective view of the present invention.
Figure 2:
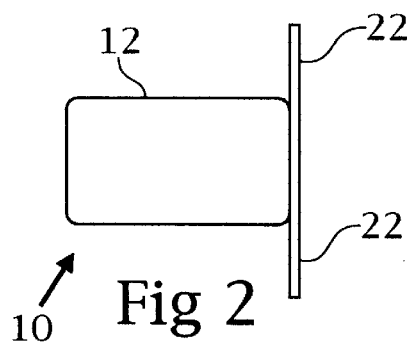
FIG. 2 is a side elevation view of the present invention.
Figure 3:
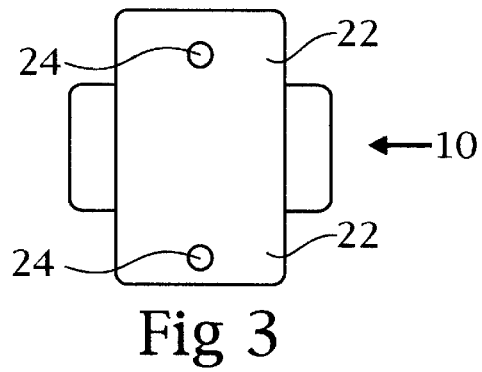
FIG. 3 is back elevation view of the present invention.

Referring now to the figures, the present invention is a pseudo arthrosis device 10 having an enclosure 12 (FIGS. 1–3). Preferably, the enclosure 12 has a cross-sectional shape which corresponds with the cross-sectional shape of the intervertebral space between two adjacent vertebrae in the spine of a vertebrate animal, preferably a human being. The enclosure 12 may be a sleeve, with or without a top and bottom, an envelope, or other configuration to meet the requirements set forth below.

The enclosure 12 is formed from a flexible permeable material as will be described. The material must be biocompatible with the human body and not be rejected, allergenic or otherwise non-compatible. Synthetic fabrics such as Dacron®, Proline Mesh® and Goretex® may be used.

Figure 4:
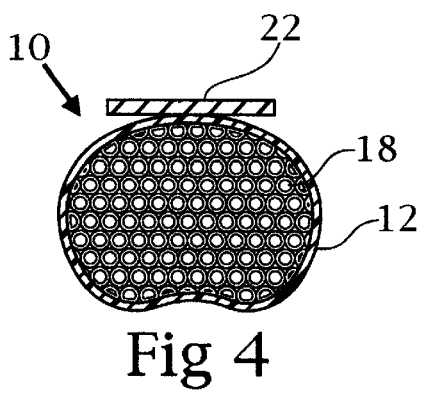
FIG. 4 is a cross-sectional view taken across the lines 4—4 of FIG. 1.
Figure 5:
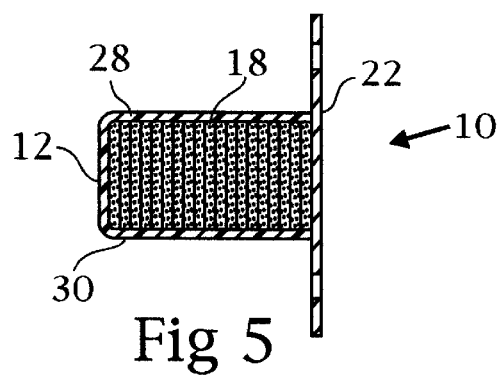
FIG. 5 is a cross-sectional view taken across the lines 5—5 of FIG. 1.
Figure 6:
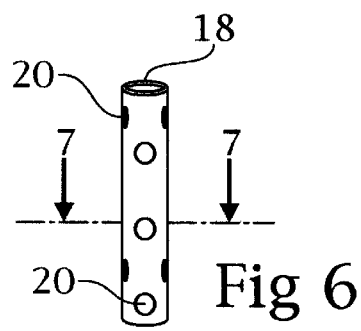
FIG. 6 is a side elevation view of a flexible member.
Figure 7:
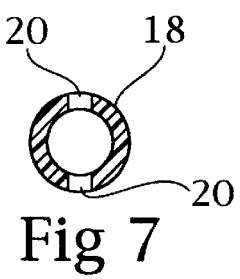
FIG. 7 is a cross-sectional view taken along the lines 7—7 of FIG. 6.

Disposed within the enclosure 12 are a plurality of compressible, flexible elongated members 18 which are packed longitudinally therein (FIGS. 4–5). It is preferred that the flexible members 18 be hollow tubes with an outer diameter ranging between 0.5 to 3.0 mm and an inner diameter ranging between 0.25 to 2.0 mm. The flexible members 18 may be solid rods. Each flexible member 18 also has a plurality of spaced-apart perforations 20 formed therein (FIGS. 6–7). A preferred wall thickness of the tubes is approximately 1 mm. The length of the rods may vary depending upon the intravertabral spacing and desired flexibility. The flexibility is also a function of wall thickness and the number and size of perforations 20 in the walls. The enclosure 12 containing the elongated members 18 may be considered as a compressible, flexible body.

Means are provided to attach the device 10 to vertebrae 16 adjacent to the intervertebral space 14. Preferably, the means is at least one tab 22 which is connected to the enclosure 12 and extends substantially perpendicularly upwardly and/or downwardly from the enclosure 12. Preferably, there is one tab 22 which extends upwardly from the enclosure 12 to the vertebra 16 immediately above the intervertebral space 14 and which also extends downwardly from the enclosure 12 to the vertebra 16 immediately below the intervertebral space 14. Alternately, there are two tabs 22, one extending upwardly and another extending downwardly. Each tab, or each portion of the single tab, 22 preferably has at least an opening 24 therein. The openings 24 may have a grommet thereabout to reinforce the opening 24. The grommet may be of titanium or a rugged material biocompatible with humans. A connector 26 or fastener is received in the opening 24 and is connected to the adjoining vertebra 16 to secure the device 10 between the adjacent vertebrae 16. The connector 26 may be a threaded screw or means known to persons skilled in the art. The tab 22 may be connected to the vertebrae by suturing. The tab(s) 22 preferably are the same material as the enclosure 12.

As shown in FIGS. 9–11, the damaged or degenerated disc is removed and the pseudo arthrosis device 10 of the present invention is inserted into the intervertebral space 14 between the adjacent vertebrae 16. The flexible members 18 within the enclosure 12 are disposed longitudinally between the adjacent vertebrae 16. The tab(s) 22 are attached to the adjacent vertebrae 16 with connectors. The tab(s) 22 is relatively small, having a size large enough to secure the enclosure 12 to the adjacent vertebrae with minimal limitation of vertebral movement.

FIGS. 12–15 show the flexing and compression of the flexible members 18 when the device 10 of the present invention is received in the patient. As the patient bends backwardly (FIG. 12) or forwardly (FIG. 13) the flexible members 18 proximal to the bend of the spine are compressed and flex while the flexible members distal to the bend of the spine are fully extended. In this manner, the vertebrae are cushioned in a manner which simulates the natural disc and the pseudo arthrosis device 10 reduces wear and tear on the vertebrae and relieves the patient of pain. FIGS. 14 and 15 show the compression when the patient leans laterally right and left. Thus, the present invention acts as a replacement disc in all postures of the patient.

Another of the features of the present invention is the permeability of the enclosure to body fiber 36. When the present invention is disposed in the spine, the body grows fibers 36 which penetrate the enclosure 12 and grow through the perforations 20 in the compressible members 18. The body fibers 36 also grow longitudinal through the hollow elongated members 18. In time, the device 10 of the present invention is incorporated into the scar tissue formed from the fibrous ingrowth of the patient to generate a natural repair. Further, the material from which the enclosure 12 is formed is biocompatible with the body.

Figure 19:
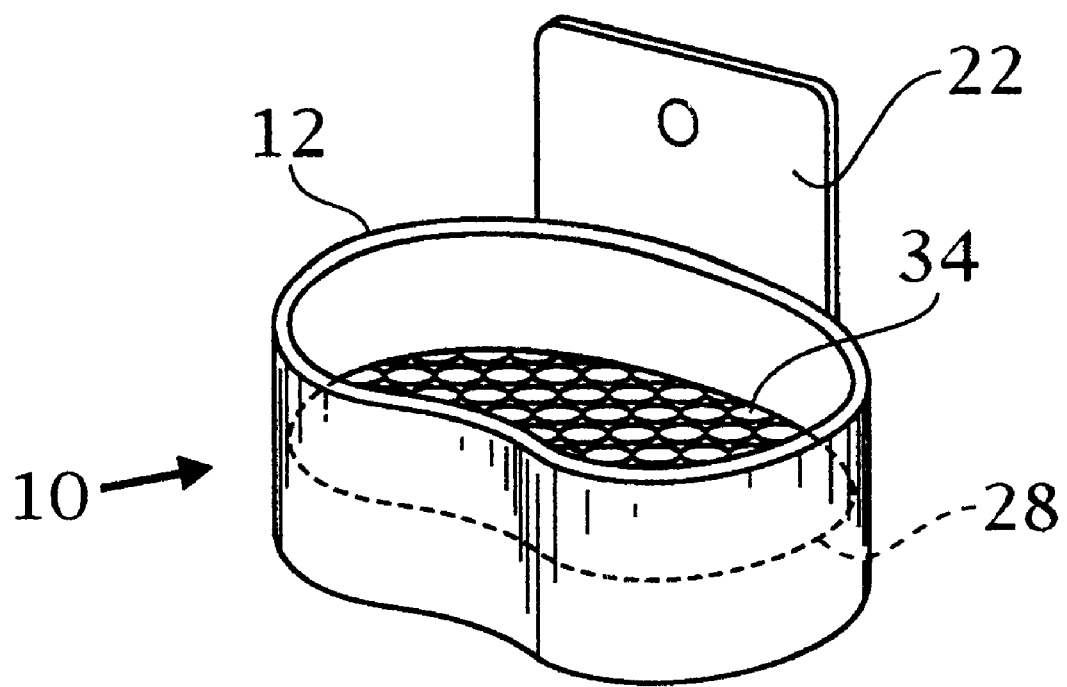
FIG. 19 is a perspective view of an alternate embodiment showing, in broken lines, a pliable retaining means within the enclosure.

It is preferred that the enclosure 12 have a top 28 and a bottom 30 to better retain therein the compressible members 18. In an alternate embodiment (FIG. 19) a pliable retaining means 32 is disposed transversely within the enclosure 12. A plurality of spaced-apart holes 34 are formed in the pliable retaining means 32. A compressible member 18 is received in each hole with a friction fit or with a means to retain each compressible member 18 in the respective hole 34. This embodiment retains the compressible member 18 in an upright packed condition, so that when the device is inserted between the adjacent vertebrae, the compressible members 18 are oriented longitudinally therebetween.

Thus, the present invention is a pseudo arthrosis device which supports adjacent vertebrae in place of a damaged spinal disc and is permeable to the growth of body fibers. The body naturally repairs itself using the present invention as a scaffold or matrix.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. A pseudo arthrosis device, comprising:
   an enclosure formed from a flexible permeable material; and
   a plurality of compressible flexible elongated hollow tubes packed longitudinally within the enclosure, wherein one or more of the tubes comprise a plurality of spaced-apart perforations.

2. The device of claim 1, wherein the device is configured to be disposed in an intervertebral space between adjacent vertebrae in a patient to allow for movement of the adjacent vertebrae relative to each other during use.

3. The device of claim 1, wherein the compressible flexible elongated hollow tubes are configured to allow body fiber ingrowth from a patient.

4. The device of claim 1, wherein the enclosure comprises a sleeve.

5. The device of claim 1, wherein the enclosure includes a top and a bottom to retain the compressible flexible elongated hollow tubes within the enclosure.

6. The device of claim 1, wherein an outer diameter of the compressible flexible elongated hollow tubes ranges from about 0.5 mm to about 3.0 mm and wherein an inner diameter of the compressible flexible elongated hollow tubes ranges from about 0.25 mm to about 2.0 mm.

7. The device of claim 1, further comprising a member coupled to the enclosure, wherein the member is configured to allow the device to be coupled to a vertebra.

8. The device of claim 1, further comprising one or more tabs coupled to the enclosure, wherein at least one of the tabs is configured to allow the device to be coupled to a vertebra, and wherein at least one of the tabs comprises an opening configured to allow a connector inserted through the opening to couple to the vertebra.

9. The device of claim 1, wherein the enclosure comprises biocompatible material.

10. The device of claim 1, wherein the compressible flexible hollow elongated tubes comprise biocompatible material.

11. A pseudo arthrosis device, comprising:
    an enclosure formed from a flexible permeable material;
    a plurality of compressible flexible elongated hollow tubes packed longitudinally within the enclosure, wherein one or more of the tubes comprise a plurality of spaced-apart perforations; and
    a pliable retaining means disposed transversely within the enclosure, the pliable retaining means having a plurality of spaced-apart holes formed therein, and wherein at least one of the hole is configured to hold one of the compressible flexible elongated hollow tubes.

12. The device of claim 11, wherein the device is configured to be disposed in an intervertebral space between adjacent vertebrae in a patient to allow for movement of the adjacent vertebrae relative to each other during use.

13. The device of claim 11, wherein the compressible flexible elongated hollow tubes are configured to allow body fiber ingrowth from a patient.

14. The device of claim 11, wherein the enclosure comprises a sleeve.

15. The device of claim 11, wherein the enclosure includes a top and a bottom to retain the compressible flexible elongate hollow tubes within the enclosure.

16. The device of claim 11, wherein an outer diameter of the compressible flexible elongated hollow tubes ranges from about 0.5 mm to about 3.0 mm and wherein an inner diameter of the compressible flexible elongated hollow tubes ranges from about 0.25 mm to about 2.0 mm.

17. The device of claim 11, further comprising a member coupled to the enclosure, herein the member is configured to allow the device to be coupled to a vertebra.

18. The device of claim 11, further comprising one or more tabs coupled to the enclosure, wherein at least one of the tabs is configured to allow the device to be coupled to a vertebra, and wherein at least one of the tabs comprises an opening configured to allow a collector inserted through the opening to couple to the vertebra.

19. The device of claim 11, wherein the enclosure comprises biocompatible material.

20. The device of claim 11, wherein the compressible flexible hollow elongated tubes comprise biocompatible material.

* * * * *